United States Patent [19]

Iwaoka

[11] Patent Number: 5,099,022

[45] Date of Patent: Mar. 24, 1992

[54] PROCESS FOR PURIFICATION OF 1,2-BIS(NICOTINAMIDO)PROPANE

[75] Inventor: Tomoyasu Iwaoka, Saitama, Japan

[73] Assignee: Chugai Seiyaku Kabushiki Kaisha, Tokyo, Japan

[21] Appl. No.: 456,794

[22] Filed: Dec. 27, 1989

[51] Int. Cl.$^5$ ............................................. C07D 213/44
[52] U.S. Cl. .................................................... 546/262
[58] Field of Search ........................................ 546/262

[56] References Cited

U.S. PATENT DOCUMENTS 4,366,161 12/1982 Mori et al. ........................... 546/262
4,910,301 3/1990 Kaplan et al. ........................ 540/222

Primary Examiner—Mary C. Lee
Assistant Examiner—Joseph K. McKane
Attorney, Agent, or Firm—Browdy and Neimark

[57] ABSTRACT

A novel process for purifying crude 1,2-bis(nicotinamido)propane obtained by the reaction of nicotinic acid with 1,2-propanediamine. This process comprises forming 1,2-bis(nicotinamido)propane dinitrate from the crude 1,2-bis(nicotinamido)propane, suspending the dinitrate in an organic solvent, adding an alkali or an alkaline solution to the suspension to dissociate the free 1,2-bis(nicotinamido)propane, extracting it from the suspension with a solvent, and removing the solvent to isolate the purified product.

According to this process, crude 1,2-bis(nicotinamido)propane can be efficiently purified to give the product having a high purity.

5 Claims, No Drawings

5,099,022

PROCESS FOR PURIFICATION OF 1,2-BIS(NICOTINAMIDO)PROPANE

FIELD OF THE INVENTION

This invention relates to a process for purification of 1,2-bis(nicotinamido)propane which has been known to have a therapeutic effect on blood and blood vessel disorders such as arteriosclerosis, thrombosis, etc., through 1,2-bis(nicotinamido)propane dinitrate.

BACKGROUND OF THE INVENTION

The present inventor previously developed a process for purifying crude 1,2-bis(nicotinamido)propane by forming 1,2-bis(nicotinamido)propane oxalate and dissociating free 1,2-bis(nicotinamido)propane from the oxalate in an aqueous solution of potassium carbonate. The thus-formed free 1,2-bis(nicotinamido)propane is then crystallized, and recrystallized or purified with the use of silica gel column chromatography as disclosed in Japanese Patent Application Public Disclosure (Kokai) No. 56-75474.

However, this purification process through the oxalate salt of 1,2-bis(nicotinamido)propane as described above has a problem in that the oxalate salt is very difficult to be recrystallized, and, thus, the desired 1,2-bis(nicotinamido)propane can only be obtained with a low purity, since free 1,2-bis(nicotinamido)propane is obtained from a mixture containing various impurities such as nicotinic acid, N-(2-ethoxycarbonylamino)-propylnicotinamide, N-(2-ethoxycarbonylamino-1-methyl)ethyl-nicotinamide, etc. The desired product thus obtained generally contains such impurities at a proportion of about 0.4 to 1.0% (ratio of area) as determined in the high performance liquid chromatography (HPLC). Further, it is very difficult to completely remove the impurities by recrystallization of 1,2-bis(nicotinamido)propane, and the recrystallized product generally contains such impurities at a proportion of about 0.1 to 0.3 (ratio of area) as determined by HPLC. It is therefore necessary to subject the product to further purification by silica gel chromatography, but such a purification procedure is disadvantageous from the standpoint of production cost and operation in the production of a large quantity of 1,2-bis(nicotinamido)propane.

As a result of extensive studies on an efficient purification process of 1,2-bis(nicotinamido)propane, the present inventor found that the above compound can be purified effectively according to the process of the present invention hereinafter described in detail, and completed the present invention.

SUMMARY OF THE INVENTION

An object of the present invention is therefore to provide an efficient process for purification of 1,2-bis(nicotinamido)propane through the dinitrate salt thereof.

The above object of the present invention can be attained by a process for purifying crude 1,2-bis(nicotinamido)propane obtained by the reaction of nicotinic acid with 1,2-propanediamine, which comprises forming 1,2-bis(nicotinamido)propane dinitrate from the crude 1,2-bis(nicotinamido)propane, suspending the dinitrate salt in an organic solvent, extracting the free 1,2-bis(nicotinamido)propane dissociated by adding an alkali or a solution of alkali to the suspension with a solvent, and removing the solvent from the extract.

DETAILED DESCRIPTION OF THE INVENTION

According to the present invention, 1,2-bis(nicotinamido)propane can be obtained by suspending nicotinic acid in an inert organic solvent and reacting nicotinic acid with an organic base and a condensing agent, and further with 1,2-propanediamine. The solvent is then removed from the resulting reaction solution to obtain crude 1,2-bis(nicotinamido)propane. The crude product is then reacted with a lower alcohol such as methanol and nitric acid to produce 1,2-bis(nicotinamido)propane dinitrate, and the resulting dinitrate salt is recrystallized from a mixture of water and a lower alcohol. The 1,2-bis(nicotinamido)propane dinitrate thus obtained was suspended in an organic solvent, and an alkali or a solution of alkali is added to the suspension. The organic layer containing the dissociated 1,2-bis(nicotinamido)propane was separated, the solvent is distilled off under reduced pressure, and the product is crystallized from a solvent and then purified by recrystallization to obtain 1,2-bis(nicotinamido)propane having a high purity.

Preferred examples of the organic solvent used for suspending nicotinic acid include methylene chloride, acetonitrile, acetone, ethyl acetate, tetrahydrofuran, etc., and methylene chloride and ethyl acetate are particularly preferred.

Preferred examples of the organic base include triethylamine, N-methylmorpholine, N-methylpiperidine, etc., with triethylamine being particularly preferred. The organic base can be generally used in an amount of from about 1 to about 3 mols per mol of nicotinic acid.

Preferred examples of the condensing agent include a chloride of carbonic acid ester such as ethyl chlorocarbonate and isobutyl chlorocarbonate, a chloride of carboxylic acid such as pivalic acid chloride, an organophosphoric acid chloride, an organosulfonic acid chloride, etc., with ethyl chlorocarbonate being particularly preferred. The condensing agent can be generally used in an amount of from about 1 to about 1.5 mols per mol of nicotinic acid.

The reaction between nicotinic acid and the condensing agent can be carried out in an inert organic solvent in the presence of the organic base at a temperature of from about $-20°$ C. to about $40°$ C., preferably from $-10°$ C. to $30°$ C., for a period of from about 10 to about 60 minutes, preferably from 20 to 30 minutes.

To the resulting reaction solution was then added 1,2-propanediamine in an amount of from about 0.45 to about 0.6 mol per mol of nicotinic acid, and the mixture is reacted at a temperature of from about $-20°$ C. to about $40°$ C., preferably from $-10°$ C. to $35°$ C., for a period of from about 30 to about 60 minutes, preferably 60 minutes. Then, a lower alcohol, e.g., methanol, was added to the reaction mixture containing the produced 1,2-bis(nicotinamido)propane or, preferably, to the reaction mixture from which the solvent has been distilled off as completely as possible, and further nitric acid is added to the mixture in an amount of from about 0.7 to about 2 mols, preferably from 1.0 to 1.9 mol, per mol of nicotinic acid, and the resulting mixture was allowed to stand at a temperature of from about $-20°$ C. to about $20°$ C., preferably at $-10°$ C., for a period of from about 1 to about 5 hours, preferably for 5 hours, to precipitate crystals thereby obtaining 1,2-bis(nicotinamido)propane dinitrate. The thus-obtained dinitrate salt can be recrystallized from a mixed solvent of water and a lower alcohol, e.g., methanol, ethanol or propanol, preferably methanol. The resulting dinitrate salt is a novel compound which has not been disclosed in literature references.

Preferred examples of the organic solvent for suspending the dinitrate salt include methylene chloride, ethyl acetate, and a lower alcohol, e.g., methanol, ethanol or propanol.

Examples of an alkali or a solution of alkali include an inorganic base such as sodium carbonate, potassium carbonate, sodium hydroxide, potassium hydroxide, etc., with an aqueous solution of sodium hydroxide being preferred.

Examples of the organic solvent used for recrystallization of 1,2-bis(nicotinamido)propane include acetone, a mixed solvent of acetone and ethanol, or toluene, with the mixed solvent of acetone and ethanol being preferred.

Thus, according to the process as described above, 1,2-bis(nicotinamido)propane having a high purity can be obtained.

The process for purification of 1,2-bis(nicotinamido)propane according to the present invention overcomes the disadvantages of the conventional purification process through 1,2-bis(nicotinamido)propane oxalate and using silica gel column chromatography, and is an excellent and efficient purification process for 1,2-bis(nicotinamido)propane having the following advantages.

(1) 1,2-Bis(nicotinamido)propane oxalate is very difficult to be recrystallized, whereas 1,2-bis(nicotinamido)propane dinitrate can be easily recrystallized from a solvent system of water and a lower alcohol whereby contamination with impurities can be prevented, as proved by a single peak observed in HPLC of the product.

(2) In removal of the salt formed after dissociation of free 1,2-bis(nicotinamido)propane, the conventional process using 1,2-bis(nicotinamido)propane oxalate should involve removal of potassium oxalate and then extraction of the free compound, whereas, in the process according to the present invention, substantially whole amount of the dinitrate salt is dissolved in an aqueous layer and thus a time-consuming purification procedure can be eliminated.

(3) The conventional process requires a purification step using silica gel chromatography which is apparently disadvantageous from the standpoint of production cost and operation, whereas the present invention does not require such a step and therefore is very efficient.

The present invention is further illustrated in greater detail by the following examples, but the present invention is not to be construed as being limited thereto.

EXAMPLE 1

Preparation of 1,2-Bis(nicotinamido)propane Dinitrate 10.7 g (0.087 mol) of nicotinic acid was suspended in 140 ml of methylene chloride, and 9.2 g (0.091 mol) of triethylamine and 9.9 g (0.091 mol) of ethyl chlorocarbonate were added to the suspension. The resulting mixture was reacted for 30 minutes at $-10°$ C. to produce a mixed acid anhydrides. Then, 3.2 g (0.043 mol) of 1,2-propanediamine was added thereto, and the mixture was reacted for 60 minutes at 30° C. Thereafter, 15.5 g (0.148 mol) of a 60% aqueous nitric acid solution and 7 ml of purified water were added to the reaction mixture, and the aqueous layer was separated. 130 ml of methanol was added to the aqueous layer, and the resulting methanolic solution was allowed to stand for 5 hours at $-10°$ C. to precipitate crystals. The crystals were filtered and recrystallized from a mixed solvent of 10 ml of water and 100 ml of methanol to obtain 9.4 g (0.023 mol) of 1,2-bis(nicotinamido)propane dinitrate having a melting point of 189.5° C.

Elementary Analysis for $C_{15}H_{18}N_6O_8$: Calc'd (%): C, 43.91; H, 4.42; N, 20.48. Found (%): C, 44.03; H, 4.44; N, 20.26.

$IR\nu_{max}^{KBr}$ cm$^{-1}$: 3300 (N—H), 1650 (C=O), 1350, 830 ($NO_3^-$).

EXAMPLE 2

Preparation of 1,2-Bis(nicotinamido)propane Dinitrate 10.7 g (0.087 mol) of nicotinic acid was suspended in 140 ml of ethyl acetate, and 9.2 g (0.091 mol) of triethylamine and 9.9 g (0.091 mol) of ethyl chlorocarbonate were added to the suspension. The resulting mixture was reacted for 30 minutes at $-10°$ C. to produce a mixed acid anhydrides. Then, 3.2 g (0.043 mol) of 1,2-propanediamine was added thereto, and the mixture was reacted for 60 minutes at 30° C. Thereafter, 15.5 g (0.148 mol) of a 60% aqueous nitric acid solution and 7 ml of purified water were added to the reaction mixture, and the aqueous layer was separated. 130 ml of methanol was added to the aqueous layer, and the resulting methanolic solution was allowed to stand for 5 hours at $-10°$ C. to precipitate crystals. The crystals were filtered and recrystallized from a mixed solvent of 10 ml of water and 100 ml of methanol to obtain 9.4 g (0.023 mol) of 1,2-bis(nicotinamido)propane dinitrate. The melting point, elementary analysis values and infrared absorption spectrum of the resulting product were found to be substantially identical to those of the product obtained in Example 1.

EXAMPLE 3

Preparation of 1,2-Bis(nicotinamido)propane 28.7 g (0.070 mol) of 1,2-bis(nicotinamido)propane dinitrate obtained in Example 1 or 2 was suspended in 165 ml of methylene chloride, and 30 ml of a 5N aqueous sodium carbonate solution was added to the suspension. The methylene chloride layer containing the dissociated 1,2-bis(nicotinamido)propane was separated, and the solvent was distilled off under reduced pressure. Then, 60 ml of acetone was added to the residue to crystallize the product which was then separated by filtration and recrystallized from a mixed solvent of 24 ml of ethanol and 80 ml of acetone to obtain 11.6 g (0.041) mol of 1,2-bis(nicotinamido)propane having a melting point of 156°–157° C.

Elementary Analysis for $C_{15}H_{16}N_4O_2$: Calculated (%): C, 63.4; H, 5.7; N, 19.7. Found (%): C, 63.2; H, 5.9; N, 19.5.

$IR\nu_{max}^{KBr}$ cm$^{-1}$: 3280 (N—H), 1660 (C=O).

EXAMPLE 4

Preparation of 1,2-Bis(nicotinamido)propane 28.7 g (0.070 mol) of 1,2-bis(nicotinamido)propane dinitrate obtained in Example 1 or 2 was suspended in 165 ml of ethyl acetate, and 30 ml of a 20% aqueous sodium hydroxide solution and 33 ml of n-propanol were added to the suspension. The ethyl acetate layer containing the dissociated 1,2-bis(nicotinamido)propane was separated, and the solvent was distilled off under reduced pressure. Then, 60 ml of acetone was added to the residue to crystallize the product which was then separated by filtration and recrystallized from a mixed solvent of 24 ml of ethanol and 80 ml of acetone to obtain 11.6 g (0.041 mol) of 1,2-bis(nicotinamido)propane. The melting point, elementary analysis values and infrared absorption spectrum of the resulting product were found to be substantially identical to those of the product obtained in Example 3.

EXAMPLE 5

Preparation of 1,2-Bis(nicotinamido)propane 28.7 g (0.070 mol) of 1,2-bis(nicotinamido)propane dinitrate was suspended in 60 ml of ethanol, and 9.2 g of potassium hydroxide was added to the suspension. The resulting ethanol layer containing the dissociated free 1,2-bis(nicotinamido)propane was separated, and the precipitated potassium nitrate was removed by filtration. After distilling off the solvent under reduced pressure, 60 ml of acetone was added to the residue to crystallize the product which was then separated by filtration and recrystallized from a mixed solvent of 24 ml of ethanol and 80 ml of acetone to obtain 11.6 g (0.041 mol) of 1,2-bis(nicotinamido)propane. The melting point, elementary analysis values and infrared absorption spectrum of the resulting product were found to be substantially identical to those of the product obtained in Example 3.

What is claimed is:

1. A process for purifying crude 1,2-bis(nicotinamido)propane obtained by the reaction of nicotinic acid with 1,2-propanediamine, which comprises forming 1,2-bis(nicotinamido)propane dinitrate from the crude 1,2-bis(nicotinamido)propane, suspending the dinitrate salt in an organic solvent, extracting the free 1,2-bis(nicotinamido)propane dissociated by adding an alkali or a solution of alkali to the suspension with a solvent, removing the solvent from the extract, and purifying the thus-obtained 1,2-bis(nicotinamido)propane.

2. A process as claimed in claim 1, wherein said organic solvent for suspending the dinitrate salt is methylene chloride, ethyl acetate or a lower alcohol.

3. A process as claimed in claim 1, wherein said alkali or the solution of alkali is sodium carbonate, potassium carbonate, sodium hydroxide or potassium hydroxide, or an aqueous solution thereof.

4. A process as claimed in claim 1, wherein said purification is carried out by recrystallization from acetone, toluene or a mixed solvent of acetone and ethanol.

5. A process for preparing pure 1,2-bis(nicotinamido)propane, comprising:

suspending nicotinic acid in an inert organic solvent and reacting said nicotinic acid with an organic base and a condensing agent, and further with 1,2-propanediamine, to produce crude 1,2-bis(nicotinamido)propane;

reacting said crude 1,2-bis(nicotinamido)propane with a lower alcohol and nitric acid to produce 1,2-bis(nicotinamido)propane dinitrate;

precipitating said 1,2-bis(nicotinamido)propane dinitrate;

suspending said 1,2-bis(nicotinamido)propane dinitrate in an organic solvent to obtain a suspension, and mixing said suspension with an alkali or a solution of alkali to effect disassociation of said dinitrate and thereby produce free 1,2-bis(nicotinamido)propane in pure form; and removing said organic solvent.

* * * * *

UNITED STATES PATENT AND TRADEMARK OFFICE
CERTIFICATE OF CORRECTION

PATENT NO. : 5,099,022
DATED : March 24, 1992
INVENTOR(S) : Tomoyasu IWAOKA It is certified that error appears in the above-identified patent and that said Letters Patent is hereby corrected as shown below:

On title page,

Insert -- [30]   Foreign Application Priority Data
          Dec. 27, 1988 [JP]   Japan...........330255 --

Signed and Sealed this

Fourteenth Day of September, 1993

Attest:

BRUCE LEHMAN

*Attesting Officer*      *Commissioner of Patents and Trademarks*